(12) United States Patent
Albrecht et al.

(10) Patent No.: US 6,316,415 B1
(45) Date of Patent: Nov. 13, 2001

(54) SULFONAMIDE INTERLEUKIN-1β CONVERTING ENZYME INHIBITORS

(75) Inventors: Hans P. Albrecht, Gorxheimertal (DE); Hamish John Allen, Boylston; Kenneth Dale Brady, Worcester, both of MA (US); William Glen Harter, Chelsea, MI (US); Catherine Rose Kostlan, Saline, MI (US); Bruce David Roth, Plymouth, MI (US); Nigel Walker, Dossenheim (DE)

(73) Assignees: BASF Aktiengesellschaft, Ludwigshafen (DE); Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/284,422

(22) PCT Filed: Oct. 9, 1997

(86) PCT No.: PCT/US97/18396

§ 371 Date: Apr. 9, 1999

§ 102(e) Date: Apr. 9, 1999

(87) PCT Pub. No.: WO98/16505

PCT Pub. Date: Apr. 23, 1998

Related U.S. Application Data

(60) Provisional application No. 60/028,313, filed on Oct. 11, 1996.

(51) Int. Cl.$^7$ .......................... A61K 31/18; A61K 38/07
(52) U.S. Cl. .......................... 514/18; 514/17; 514/601; 530/330
(58) Field of Search .................. 514/17, 18, 601; 530/330

(56) References Cited

U.S. PATENT DOCUMENTS 5,656,627    8/1997    Bemis et al. ............... 514/221

FOREIGN PATENT DOCUMENTS

| 0 496 378 | 1/1992 | (EP) . |
|---|---|---|
| 0 519 748 | 12/1992 | (EP) . |
| 2 292 149 | 2/1996 | (GB) . |
| 93/14066 | 7/1993 | (WO) . |
| 95/05192 | 2/1995 | (WO) . |
| 95/26958 | 10/1995 | (WO) . |
| 95/33751 | 12/1995 | (WO) . |
| 95/35308 | 12/1995 | (WO) . |
| 97/22619 | 6/1997 | (WO) . |

OTHER PUBLICATIONS

A.M.M. Mjalli, et al., *Bioorganic and Medicinal Chemistry Letters*, "Activated Ketones as Potent Reversible Inhibitors of Interleukin–1B Converting Enzyme", vol. 4, No. 16, 1994, pp 1965–1968.

A.M.M. Mjalli, et al., *Bioorganic and Medicinal Chemistry Letters*, "Inhibition of Interleukin–1B Converting Enzyme by N–acyl–aspartic acid ketones" vol. 5, No. 13, 1995, pp. 1405–1408.

*Primary Examiner*—Michael Borin
(74) *Attorney, Agent, or Firm*—John D. Conway

(57) ABSTRACT

The present invention relates to compounds that are inhibitors of interleukin-1β converting enzyme that have the Formula (I). This invention also relates to a method of treatment of stroke, reperfusion injury, Alzheimer's disease, shigellosis, inflammatory diseases, and septic shock and to a pharmaceutically acceptable composition that contains a compound that is an inhibitor of interleukin-1β converting enzyme.

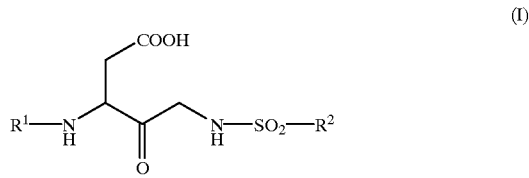

28 Claims, No Drawings

SULFONAMIDE INTERLEUKIN-1β CONVERTING ENZYME INHIBITORS

This application claims priority of provisional application 60/028,313, filed Oct. 11, 1996.

FIELD OF THE INVENTION

This invention relates to compounds that are inhibitors of interleukin-1β converting enzyme. This invention also relates to a method of treatment of stroke, reperfusion injury, Alzheimer's disease, shigellosis, and inflammatory diseases and to a pharmaceutically acceptable composition that contains a compound that is an inhibitor of interleukin-1β converting enzyme (Caspase-1).

BACKGROUND OF THE INVENTION

The compounds of the present invention are inhibitors of interleukin-1β converting enzyme (ICE) and are useful in treating diseases in which interleukin-1 plays a role.

ICE acts on pro-interleukin-1β (pro-IL-1β) to produce interleukin-1β (IL-1β), which is an inflammatory cytokine. In addition, ICE (Caspase-1) regulates at least four cytokines. ICE activates IL-β and IL-18, and indirectly regulates the production of IL1 and IFNγ. Several diseases are associated with excessive interleukin-1 activity. Examples of diseases in which interleukin-1 is involved include, but are not limited to, inflammatory diseases such as rheumatoid arthritis and inflammatory bowel disease, and neuroinflammatory disorders such as stroke. Other diseases include septic shock, reperfusion injury, Alzheimer's disease, and shigellosis.

Agents that modulate IL-1β activity have been shown to have beneficial in vivo effects. For example, compounds that are interleukin-1 receptor antagonists have been shown to inhibit ischemic and excitotoxic damage in rat brains. See, for example, Relton J. K., et al., *Brain Research Bulletin*, 1992;29:243–246. Additionally, ICE inhibitors were shown to reduce inflammation and pyrexia in rats. See Elford P. R., et al., *British Journal of Pharmacology*, 1995; 115:601–606.

The compounds of the present invention are also inhibitors of other cysteine proteases in the ICE family. Many of these proteases have only recently been described in the literature. While the nomenclature is still unresolved, the following proteases are representative members of this class of enzymes; Ich-2 (also called Tx or ICErel-II), ICErel-III, Ich-I (also called Nedd-2), CPP-32 (also called apopain and yama), Mch-2, Mch-3 (also called ICE-lap3, CMH-1), and Ced-3. See Henkart P. A., *Immunity*, 1996;4:195–201. It is recognized that members of this enzyme family play key biological roles in both inflammation and apoptosis (programmed cell death). In particular, Caspase-4 can activate IL-1β and IL-18. It has been shown that a murine homolog of Caspase-4 can activate ICE. Thus, inhibition of Caspase-4 will act to inhibit ICE. See Thornberry N. A., et al., *Perspectives in Drug Discovery and Design*, 1994;2:389–399.

In addition to its effects on IL-1β production, ICE has been shown to play a role in the production of the inflammatory mediator interferon-γ (Ghayur, et al., *Nature*, 1997;386(6625):619–623). ICE processes the inactive pro-form of interferon-γ inducing factor (IGIF; Interleukin-18) to active IGIF, a protein which induces production of interferon-γ by T-cells and natural killer cells. Interferon-γ has been implicated in the pathogenesis of diseases such as inflammatory disorders and septic shock. Therefore, ICE inhibitors would be expected to have beneficial effects in such disease states by effects on interferon-γ.

Recently, the nomenclature of these cysteine proteases in the ICE family (also known as Caspases with ICE being known as Caspase-1) has been further defined. The following proteases are representative members of this class of enzymes using the nomenclature described in Alnemri, et al., *Cell*, 1996;87:171: Caspase-2 (also known as Ich-1); Caspase-3 (also known as CPP32, Yama, and apopain); Caspase-4 (also known as TX, Ich-2, and ICE rel-II); Caspase-5 (also known as ICE rel-III); Caspase-6 (also known as Mch2); Caspase-7 (also known as Mch3); Caspase-8 (also known as FLICE and Mch5); Caspase-9 (also known as ICE-LAP6 and Mch6); Caspase-10 (also known as Mch4).

SUMMARY OF THE INVENTION

The present invention provides compounds of Formula I

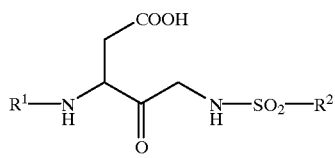

wherein $R^1$ is

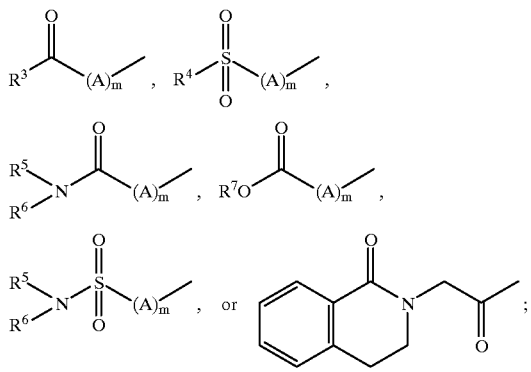

$R^3$ is hydrogen,
  $C_1$–$C_6$ alkyl,
  —$(CH_2)_n$ aryl, or
  —$(CH_2)_n$ heteroaryl;
$R^4$ is $C_1$–$C_6$ alkyl,
  —$(CH_2)_n$ aryl, or
  —$(CH_2)_n$ heteroaryl;
$R^5$ and $R^6$ are each independently hydrogen,
  $C_1$–$C_6$ alkyl,
  —$(CH_2)_n$ aryl, or
  —$(CH_2)_n$ heteroaryl;
$R^7$ is $C_1$–$C_6$ alkyl,
  —$(CH_2)_n$ aryl, or
  —$(CH_2)_n$ heteroaryl;
each n is independently 0 to 6;
each m is independently 0, 1, 2, or 3;
A is alanine, leucine, isoleucine, proline, phenylalanine, glycine, tyrosine, serine, threonine, tryptophan, cysteine, methionine, valine, asparagine, glutamine, aspartic acid, lysine, glutamic acid, arginine, or histidine; each $R^Q$ is independently hydrogen or $C_1$–$C_6$ alkyl;
—$R^2$ is —$(CH_2)_n$—Z; and Z is aryl, heteroaryl, cycloalkyl, $C_1$–$C_6$ alkyl,

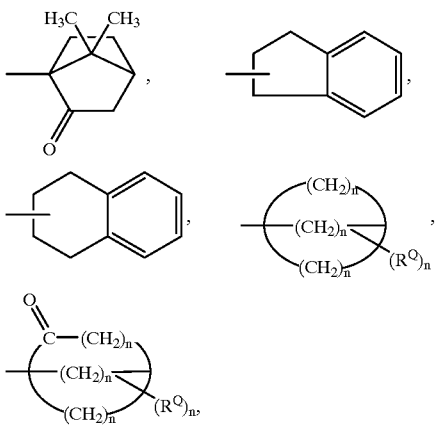

fluorenyl, substituted fluorenyl, substituted aryl, substituted heteroaryl, or substituted cycloalkyl, and the pharmaceutically acceptable salts, esters, amides, and prodrugs thereof.

In a preferred embodiment of the compounds of Formula I, $R^1$ is

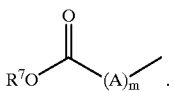

In another preferred embodiment of the compounds of Formula I $R^1$ is

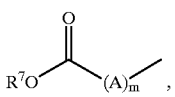

m is 0, and $R^7$ is —$(CH_2)_n$ aryl.

In another preferred embodiment of the compounds of Formula I, $R^1$ is

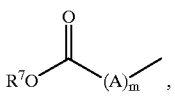

m is 0, and $R^7$ is —$CH_2$ aryl.

In another preferred embodiment of the compounds of Formula I, $R^2$ is —$(CH_2)_n$ aryl.

In another preferred embodiment of the compounds of Formula I, aryl is phenyl or naphthyl.

In another preferred embodiment of the compounds of Formula I, $R^2$ is —$(CH_2)_n$-cycloalkyl.

In another preferred embodiment of the compounds of Formula I, $R^1$ is

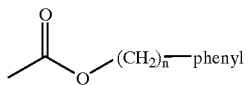

or —$SO_2$-phenyl.

In another preferred embodiment of the compounds of Formula I, $R^2$ is

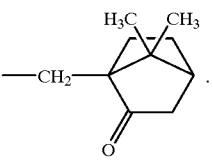

In another preferred embodiment of Formula I, $R^2$ is

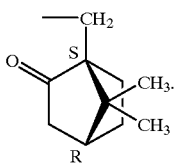

The present invention also provides compounds of the Formula I

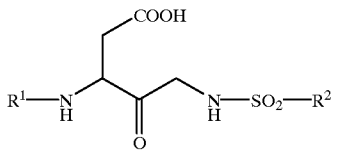

wherein $R^2$ is —$CH_2CH_2$-aryl, —$CH_2$-cycloalkyl, —$CH_2CH_2$-cycloalkyl, or —$CH_2CH_2$-heteroaryl;

$R^1$ is

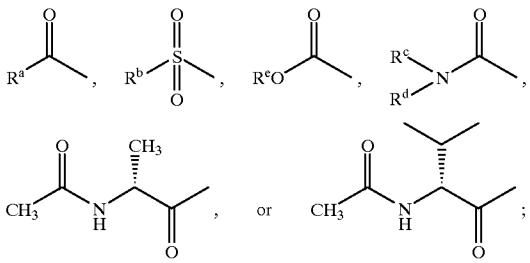

$R^a$ is —$(CH_2)_n$-aryl or —$(CH_2)_n$ heteroaryl;
$R^b$ is aryl or heteroaryl;
$R^c$ is —$CH_2$ aryl or aryl;
$R^d$ is hydrogen or $C_1$–$C_6$ alkyl;
$R^e$ is —$CH_2$ aryl or —$CH_2$ heteroaryl; and the pharmaceutically acceptable salts, esters, amides, and prodrugs thereof In a preferred embodiment of the compounds of Formula I, $R^1$ is

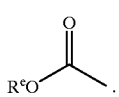

In another preferred embodiment of the compounds of Formula I, R¹ is

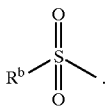

In another preferred embodiment of the compounds of Formula I, R$^e$ is —(CH$_2$)$_n$ aryl.

In another preferred embodiment of the compounds of Formula I, aryl is phenyl or naphthyl.

In another preferred embodiment of the compounds of Formula I, R$^b$ is aryl.

In a preferred embodiment, the present invention provides the compounds:

3-Benzyloxycarbonylamino-4-oxo-5-(2-phenylethanesulfonylamino)-pentanoic acid;

3-Benzyloxycarbonylamino-4-oxo-5-(3-phenyl-propane-1-sulfonylamino)-pentanoic acid;

3-Benzyloxycarbonylamino-4-oxo-5-phenylmethanesulfonyl-amino-pentanoic acid;

5-Benzenesulfonylamino-3-benzyloxycarbonylamino-4-oxo-pentanoic acid;

3-Benzyloxycarbonylamino-5-methanesulfonylamino-4-oxo-pentanoic acid;

3-Benzyloxycarbonylamino-5-(naphthalene-1-sulfonylamino)-4-oxo-pentanoic acid;

3-Benzyloxycarbonylamino-5-(2-cyclohexyl-ethanesulfonylamino)-4-oxo-pentanoic acid;

3-Benzyloxycarbonylamino-5-(2-naphthalen-1-yl-ethanesulfonylamino)-4-oxo-pentanoic acid;

3-Benzyloxycarbonylamino-5-(7,7-dimethyl-2-oxo-bicyclo[2.2.1]hept-1-(R)-ylmethanesulfonylamino-4-oxo-pentanoic acid;

3-Benzyloxycarbonylamino-5-(indan-1-ylmethanesulfonylamino)4-oxo-pentanoic acid;

3-Benzyloxycarbonylamino-5-(9-fluoro-9H-fluoren-9-ylmethanesulfonylamino)-4-oxo-pentanoic acid;

3-Benzyloxycarbonylamino-5-(7,7-dimethyl-2-oxo-bicyclo[2.2.1]hept-1-(S)-ylmethanesulfonylamino)-4-oxo-pentanoic acid;

3-[2-(2-Benzyloxycarbonylamino-3-methyl-butyrylamino)-propionylamino]-4-oxo-5-(2-phenyl-ethanesulfonylamino)-pentanoic acid;

3-[2-(2-Benzyloxycarbonylamino-4-carboxy-butyrylamino)-3-methyl-butyrylamino]-4-oxo-5-(2-phenyl-ethanesulfonylamino)-pentanoic acid;

3-{2-[4-Carboxy-2-(3-phenyl-propionylamino)-butyrylamino]-3-methyl-butyrylamino}-4-oxo-5-(2-phenyl-ethanesulfonylamino)-pentanoic acid;

3-(2-{2-[2-Acetylamino-3-(4-hydroxy-phenyl)-propionylamino]-4-carboxy-butyrylamino}-3-methyl-butyrylamino)-4-oxo-5-(2-phenyl-ethanesulfonylamino)-pentanoic acid (Sequence ID No. 1);

3-(2-Acetylamino-3-methyl-butyrylamino)-5-(7,7-dimethyl-2-oxo-bicyclo[2.2.1]hept-1-(S)-ylmethanesulfonylamino)-4-oxo-pentanoic acid;

3-(2-Acetylamino-propylamino)-5-(7,7-dimethyl-2-oxo-bicyclo[2.2.1]hept-1-(S)-ylmethanesulfonylamino)-4-oxo-pentanoic acid;

3-[2-(2-Benzyloxycarbonylamino-3-methyl-butyrylamino)-propionylamino]-5-(7,7-dimethyl-2-oxo-bicyclo[2.2.1]hept-1-ylmethanesulfonylamino)4-oxo-pentanoic acid;

3{2-[4-Carboxy-2-(3-phenyl-propionylamino)-butyrylamino]-3-methyl-butyrylamino}-5-(7,7-dimethyl-2-oxo-bicyclo[2.2.1]hept-1-ylmethanesulfonylamino)-4-oxo-pentanoic acid;

3-(2-{2-[2-Acetylamino-3-(4-hydroxy-phenyl)-propionylamino]-4-carboxy-butyrylamino}-3-methyl-butyrylamino)-5-(7,7-dimethyl-2-oxo-bicyclo[2.2.1]hept-1-ylmethanesulfonylamino)-4-oxo-pentanoic acid (Sequence ID No. 2);

3-[2-(2-Benzyloxycarbonylamino-4-carboxy-butyrylamino)-3-methyl-butyrylamino]-5-(7,7-dimethyl-2-oxo-bicyclo[2.2.1]hept-1-ylmethanesulfonylamino)-4-oxo-pentanoic acid;

3-(1, 2, 3, 4-tetrahydro-1-oxo-isoquinoline-2-yl)-acetanino-5-benzenesulfonylamino-4-oxo-pentanoic acid;

(S)-5-(Bicyclo[2.2.1]hept-1-ylmethanesulfonylamino)-4-oxo-3-[2-(1-oxo-3,4-dihydro-1H-isoquinolin-2-yl)-acetylamino]-pentanoic acid;

(S)-4-Oxo-3-[2-(1-oxo-3,4-dihydro-1H-isoquinolin-2-yl)-acetylamino]-5-(2-phenyl-ethanesulfonylamino)-pentanoic acid; and 4-Oxo-3-[2-(1-oxo-3,4-dihydro-1H-isoquinolin-2-yl)-acetylamino]-5-phenylethanesulfonylamino-pentanoic acid.

Also provided is a method of inhibiting interleukin-1β converting enzyme, the method comprising administering to a patient in need of inhibition of interleukin-1β converting enzyme a therapeutically effective amount of a compound of Formula I or II.

Also provided is a method of inhibiting Caspase4, the method comprising administering to a patient in need of Caspase-4 inhibition a Caspase-4 inhibiting amount of a compound of Formula I or II.

Also provided is a method of treating stroke, the method comprising administering to a patient having a stroke or having had a stroke a therapeutically effective amount of a compound of Formula I or II.

Also provided is a method of treating inflammatory diseases, the method comprising administering to a patient having an inflammatory disease a therapeutically effective amount of a compound of Formula I or II.

In a preferred embodiment, the inflammatory disease is arthritis.

In another preferred embodiment, the inflammatory disease is inflammatory bowel disease.

Also provided is a pharmaceutically acceptable composition that contains a compound of Formula I or II.

Also provided is a method of treating septic shock, the method comprising administering to a patient having septic shock a therapeutically effective amount of a compound of Formula I or II.

Also provided is a method of treating reperfusion injury, the method comprising administering to a patient having reperfusion injury a therapeutically effective amount of a compound of Formula I or II.

Also provided is a method of treating Alzheimer's disease, the method comprising administering to a patient having Alzheimer's disease a therapeutically effective amount of a compound of Formula I or II.

Also provided is a method of treating shigellosis, the method comprising administering to a patient having shigellosis a therapeutically effective amount of a compound of Formula I or II.

The present invention provides compounds of the Formula II.

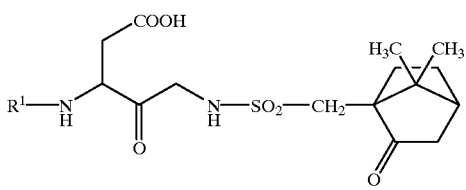

II wherein
R$^1$ is

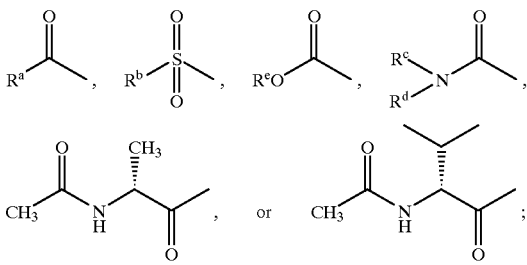

R$^a$ is —(CH$_2$)$_n$-aryl or —(CH$_2$)$_n$ heteroaryl;
R$^b$ is aryl or heteroaryl;
R$^c$ is —CH$_2$ aryl or aryl;
R$^d$ is hydrogen or C$_1$–C$_6$ alkyl;
R$^e$ is —CH$_2$ aryl or —CH$_2$ heteroaryl; and the pharmaceutically acceptable salts, esters, amides, and prodrugs thereof.

In a preferred embodiment of the compounds of Formula II, R$^1$ is

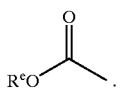

In a preferred embodiment of the compounds of Formula II, R$^1$ is

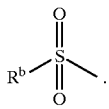

In another preferred embodiment of the compounds of Formula II, R$^e$ is —(CH$_2$)$_n$ aryl.

In another preferred embodiment of the compounds of Formula II, aryl is phenyl or naphthyl.

In another preferred embodiment of the compounds of Formula II, R$^b$ is aryl.

DETAILED DESCRIPTION OF THE INVENTION

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "cycloalkyl" means a cyclic alkyl group having 3 to 8 carbons. The cycloalkyl group can be fused to one or more aryl or heteroaryl groups. Representative examples are cyclopentyl, cyclohexyl, 1- or 2-indanyl, 1- or 2-tetralinyl, and 9-fluorenyl. The term "cycloalkyl" includes bicycloalkyl and substituted bicycloalkyl. Suitable substituents are defined with respect to aryl below.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "aryl" means an aromatic hydrocarbon. Representative examples of aryl groups include phenyl, naphthyl, and biphenyl.

The term "heteroatom" includes oxygen, nitrogen, sulfur, and phosphorus.

The term "heteroaryl" means an aryl group wherein one or more carbon atom of the aromatic hydrocarbon has been replaced with a heteroatom. Examples of heteroaryl groups include furan, thiophene, pyrrole, thiazole, pyridine, pyrimidine, pyrazine, benzofuran, indole, coumarin, quinoline, isoquinoline, carbazole, and naphthyridine.

The aryl or heteroaryl groups may be substituted with one or more substituents, which can be the same or different. Examples of suitable substituents include alkyl, alkoxy, thioalkoxy, hydroxy, halogen, trifluoromethyl, amino, alkylamino, dialkylamino, —(CH$_2$)$_n$OH, —NO$_2$, —CN, —CO$_2$H, —CO$_2$alkyl, —SO$_3$H, —CHO, —COalkyl, —CONH$_2$, —CONH-alkyl, —CONHR$^q$, —CON(alkyl)$_2$, —(CH$_2$)$_n$-NH$_2$, —(CH$_2$)$_n$-NH-alkyl, —NHR$^q$, or —NHCOR$^q$, where n is 1 to 5 and R$^q$ is hydrogen or alkyl. It is intended that the terms "aryl" and "heteroaryl" include unsubstituted as well as substituted aryl and heteroaryl groups. It is also intended that the substituents on the aryl or heteroaryl groups include other cyclic compounds that are fused to the aryl or heteroaryl groups, typically by adjacent carbon atoms. For example, a phenyl group may be fused with a cyclohexane group.

The symbol "—" means a bond.

The compounds of Formula I or II can be administered to a patient either alone or as part of a pharmaceutically acceptable composition. The compositions can be administered to patients such as humans and animals either orally, rectally, parenterally (intravenously, intramuscularly, or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, and sesame oil, glycerol, tetrahydrofurfuryl alcohol, polyethyleneglycols, and fatty acid esters of sorbitan or mixtures of these substances, and the like.

Besides such inert diluents, the composition can also include adjuvants, such as wetting agents, emulsifying, and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders and solutions are also contemplated as being within the scope of this invention.

The compounds of the present invention can be administered to a patient at dosage levels in the range of about 0.1 to about 1,000 mg per day. For a normal human adult having a body weight of about 70 kg, a dosage in the range of about 0.01 to about 100 mg/kg of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free-base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts and the like. These may include cations based on the alkali and alkaline earth metals, such as sodium, lithium, potassium, calcium, magnesium, and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.,* 1977; 66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines, and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds; ie, each asymmetric carbon can have either the R or S configuration. It is contemplated that all stereoisomeric forms of the compounds as well as mixtures thereof, including racemic mixtures, form part of this invention.

The compounds of the present invention are administered to a patient in need of ICE inhibition. In general, patients in need of ICE inhibition are those patients having a disease or condition in which interleukin-1 plays a role. Examples of such diseases include, but are not limited to, inflammatory diseases such as rheumatoid arthritis, inflammatory bowel disease, and neuroinflammatory disorders such as stroke and septic shock. Other diseases include reperfusion injury, Alzheimer's disease, and shigellosis.

A "therapeutically effective amount" is an amount of a compound of Formula I or II that when administered to a patient having a disease that can be treated with a compound of Formula I or II ameliorates a symptom of the disease. A therapeutically effective amount of a compound of Formula I or II is readily determined by one skilled in the art by administering a compound of Formula I or II to a patient and observing the results.

The following examples illustrate particular embodiments of the invention and are not intended to limit the scope of the specification and claims in any manner.

Compounds of the current invention can be prepared generally by converting the appropriate starting sulfonamide 1 to Boc sulfonamide 2 using a reagent such as di-tert-butyl dicarbonate. Boc sulfonamide 2 may then be reacted with the appropriately substituted aspartic acid bromomethylketone β tert-butyl ester 3 in the presence of a base, followed by treatment with acid to give the desired product 4.

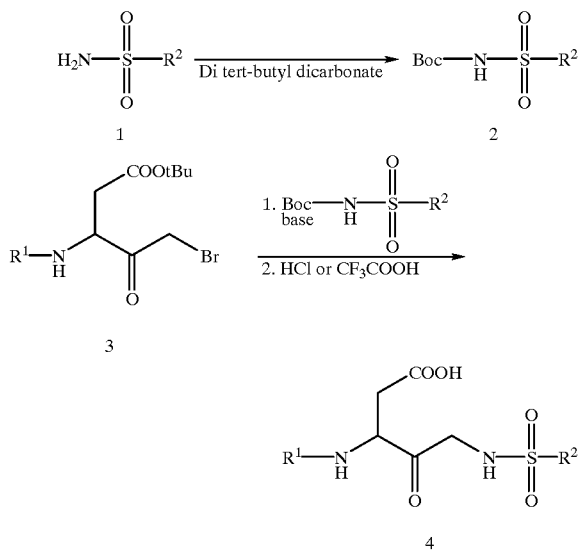

Alternatively, compounds of the current invention can be prepared generally by reaction of the appropriately substituted aspartic acid aldehyde 1 with nitromethane in the presence of a base such as potassium tert-butoxide to give nitro alcohol 2. Reduction of 2 to the amine 3, followed by reaction with the appropriate sulfonyl chloride gives 4 which may be oxidized to the ketone 5 with a reagent such as Dess Martin periodinane or by a Swern oxidation. Acidic deprotection of the t-butyl ester with HCl or trifluoroacetic acid gives the desired product 6.

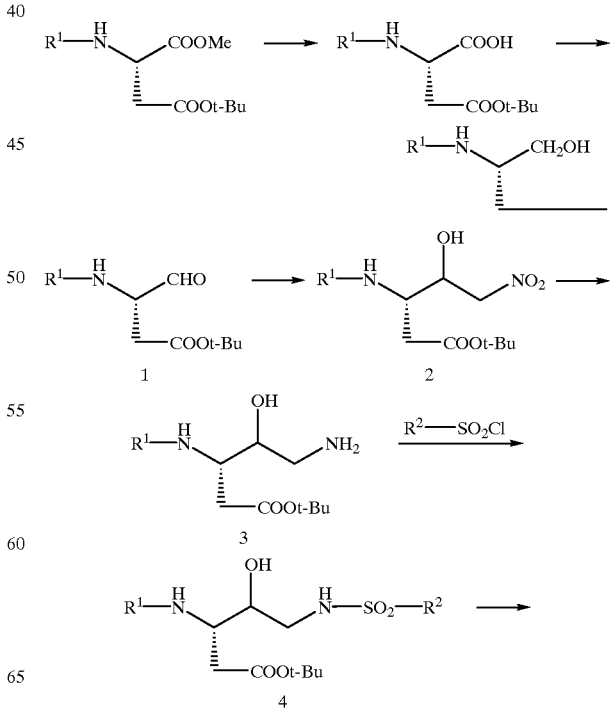

-continued

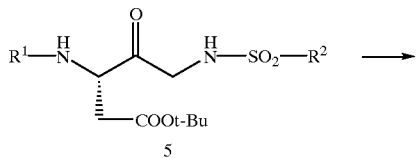

EXAMPLE 1a

1,1-Dimethylethyl[(2-phenylethyl)sulfonyl]carbamate

A solution of di-tert-butyldicarbonate (1.07 g) in methylene chloride (3 mL) was added dropwise to a solution of 2-phenylethanesulfonamide (0.78 g), triethylamine (0.48 g), and DMAP (dimethylamino-pyridine) (0.012 g) in methylene chloride (10 mL). The reaction mixture was stirred for 3 hours at ambient temperature and the solvent was evaporated. The resulting oil was taken up in ethyl acetate, washed with 5% HCl, water, and then brine. The organic layer was dried over sodium sulfate, filtered, and the solvent evaporated. The resulting oil was purified by flash column chromatography on silica (1% ether/10% hexane/methylene chloride gradient to 20% ether/10% hexane/methylene chloride) to yield 1,1-dimethylethyl[(2-phenylethyl)sulfonyl]carbamate (0.87 g), melting point (mp) 99–102° C., which was used in the next step without further purification.

The following compounds were prepared according to the procedure of Example 1a from the corresponding sulfonamides:

EXAMPLE 1b

1,1-Dimethylethyl[(3-phenylpropyl)sulfonyl]carbamate, mp 59–62° C.

EXAMPLE 1c

1,1-Dimethylethyl[(phenylmethyl)sulfonyl]carbamate, mp 90–94° C. (dec).

EXAMPLE 1d

Tert-butyl[benzenesulfonyl]carbamate

MS (AP−):256. CHN Calculated: C, (51.35%); H, (5.88%), N, (5.44%); S, (12.46%). Found: C, (51.41%); H, (5.59%); N, (5.40%); S, (12.44%).

EXAMPLE 1e

Tert-butyl[methanesulfonyl]carbamate

MS (AP−): 194. CHN Calculated: C, (36.91%); H, (6.71%); N, (7.17%); S, (16.42%). Found: C, (36.96%); H, (6.54%); N, (7.08%); S, (16.39%).

EXAMPLE 1f

Tert-butyl[naphthalene-1-sulfonyl]carbamate

MS (AP−): 306. CHN Calculated: C, (58.62%); H, (5.57%); N, (4.56%); S, (10.43%). Found: C, (58.54%); H, (5.40%); N, (4.44%); S, (10.40%).

EXAMPLE 1g

Tert-butyl[2-cyclohexyl-ethanesulfonyl]carbamate

MS (AP−): 290. CHN Calculated: C, (53.58%); H, (8.65%); N, (4.81%); S (11.00%). Found: C, (53.64%); H, (8.58%); N, (4.89%); S (11.26%).

EXAMPLE 1h

Tert-butyl[2-naphthalen-1-yl-ethanesulfony]carbamate

NMR (CDCl$_3$): 7.98(d, 1H), 7.89 (d, 1H), 7.79 (d, 1H), 7.6–7.3 (m, 4H), 6.85 (br, 1H), 3.83–3.77 (m, 2H), 3.64–3.60 (m, 2H), 1.44 (s, 9H).

EXAMPLE 1i

Tert-butyl[7,7-dimethyl-2-oxo-bicyclo[2.2.1]hept-1-ylmethanesulfonyl]carbamate MS (AP+): base peak 276 (parent with loss of isobutylene). CHN Calculated: C, (54.36%); H, (7.60%); N, (4.23%). Found: C, (54.64%); H, (7.62%); N, (3.98%).

EXAMPLE 1j

Tert-butyl[indan-1-ylmethanesulfonyl]carbamate

IR (cm$^{-1}$): 3246, 3232, 2980, 2937, 1740, 1436, 1350, 1243, 1137, 9176, 830, 757. MS (AP+): 310.

EXAMPLE 1k

Tert-butyl[9-fluoro-9H-fluoren-9-ylmethanesulfonyl]carbamate

MS (AP−): 376. CHN Calculated: C, (60.46%); H, (5.34%); N, (3.71%); S, (8.50%); F, (5.03%). Found: C, (60.19%); H, (5.40%); N, (3.64%); S, (8.33%); F, (4.89%).

EXAMPLE 2a

3-Benzyloxycarbonylamino-4-oxo-5-(2-phenylethane-sulfonylamino)-pentanoic acid To a solution of 1,1-dimethylethyl[(2-phenylethyl)sulfonyl]carbamate (0.28 g) in dry DMF (dimethylformamide) (2 mL) was added potassium tert-butoxide (0.12 g) and the resulting solution was added dropwise to an ice-cooled solution of 3-benzyloxycarbonylamino-5-bromo-4-oxo-pentanoic acid 1,1-dimethylethyl ester (0.32 g) in DMF (2 mL). The reaction mixture was stirred at room temperature for 24 hours, poured into water (100 mL), and the resulting solution was neutralized with dilute aqueous NH$_4$Cl. The product was extracted into ether (3×50 mL) and the combined organic layers were washed with water, dilute Na$_2$S$_2$O$_3$, and then brine. The solution was dried over sodium sulfate, filtered, and the solvent was evaporated to give the crude intermediate ester (0.49 g) as a yellow oil.

The oil was dissolved in methylene chloride (10 mL) and trifluoroacetic acid (10 mL) and the resulting solution was stirred at room temperature for 6 hours. The solvent was evaporated to give a yellow oil which was purified by column chromatography (silica; 1% acetone/1% formic acid/methylene chloride gradient to 20% acetone/1% formic acid/methylene chloride) and recrystallized from ether/hexane to give 3-benzyloxycarbonylamino4-oxo-5-(2-phenyl -ethanesulfonylamino)-pentanoic acid (0.04 g), mp 100–101° C.

(NMR [CD$_3$OD], ppm) 7.4–7.1 (m, 10H), 5.1 (s, 2H), 4.5 (t, 1H), 4.35 (d, 1H), 4.15 (d, 1H), 3.3–3.0 (m, 4H), 2.9–2.7 (m, 2H).

The following compounds were prepared according to the procedure of Example 2a from the corresponding Boc protected sulfonamides:

EXAMPLE 2b

3-Benzyloxycarbonylamino-4-oxo-5-(3-phenylpropane-1-sulfonylamino)-pentanoic acid, mp 96–104° C.

(NMR [CD$_3$OD], ppm) 7.4–7.1 (m, 10H), 5.11 (s, 2H), 4.5 (t, 1H), 4.3 (d, 1H), 4.1(d, 1H), 3.05–2.6 (m, 6H), 2.2–2.0 (m, 2H).

EXAMPLE 2c

3-Benzyloxycarbonylamino-4-oxo-5-phenylmethanesulfonyl-amino-pentanoic acid, mp 160–164° C.

(NMR [CD$_3$OD], ppm) 7.5–7.2 (m, 10), 5.13 (s, 2H), 4.47 (t, 1H), 4.30 (s, 2H), 4.20(d, 1H), 4.0 (d, 1H), 2.9–2.7 (m, 2H).

EXAMPLE 2d

5-Benzenesulfonylamino-3-benzyloxycarbonylamino-4-oxo-pentanoic acid

MS (AP+): 421. CHIN Calculated: C, (54.28%); H, (4.79%); N, (6.66%); S, (7.63%). Found: C, (54.19%); H, (4.85%); N, (6.47%); S, (7.36%). Water (0.10%).

EXAMPLE 2e

3-Benzyloxycarbonylamino-5-methanesulfonylamino-4-oxo-pentanoic acid

NMR (ppm, CD$_3$OD): 7.4–7.2 (m, 5H), 5.48 (s, 2H), 4.51 (t, 1H), 4.4–4.1 (dd, 2H), 2.9–2.7 (m, 5H). CHN Calculated: C, (53.58%); H, (8.65%); N, (4.81%); S, (11.00%). Found: C, (53.64%); H, (8.58%); N, (4.89%); S, (11.26%).

EXAMPLE 2f

3-Benzyloxycarbonylamino-5-(naphthalene-1-sulfonylamino)-4-oxo-pentanoic acid

MS (AP+): 471. IR (KBr, cm$^{-1}$): 3347, 2928, 1717, 1508, 1327, 1162, 1134, 772, 589.

EXAMPLE 2g

3-Benzyloxycarbonylamino-5-(2-cyclohexyl-ethanesulfonylamino)-4-oxo-pentanoic acid NMR (ppm, CD$_3$OD): 7.4–7.2 (m, 5H), 5.12 (s, 2H), 4.50 (t, 1H), 4.4–4.2 (d, 1H), 4.2–4.0 (d, 1H), 3.1–2.7 (m,4H), 1.8–1.6 (m, 8H), 1.4–1.1 (m, 5H), 1.0–0.8 (m,2H).

EXAMPLE 2h

3-Benzyloxycarbonylamino-5-(2-naphthalen-1-yl-ethanesulfonylamino)-4-oxo-pentanoic acid NMR (ppm, CD$_3$OD) 8.11 (d, 1H), 7.88 (d, 1H), 7.77 (d, 1H), 7.6–7.2 (m, 9H), 5.06 (s, 2H), 4.51 (t, 1H), 4.4 (d, 1H), 4.2 (d, 1H), 3.7–3.5 (m, 2H), 3.4–3.3 (m) 2.9–2.7 (m, 2H).

IR (KBr, cm$^{-1}$): 3307, 2926, 1735, 1685, 1544, 1398, 1322, 1275, 1136, 778, 698.

EXAMPLE 2i

3-Benzyloxycarbonylamino-5-(7,7-dimethyl-2-oxo-bicyclo]2.2.1]hept-1-(R) -ylmethanesulfonylamino)-4-oxo-pentanoic acid IR (LF+CHCl$_3$, cm$^{-1}$): 3314, 2960, 1730.5, 1525, 1329, 1217, 1146, 1052, 754. NMR (CD$_3$OD, ppm): 7.4–7.2 (m, 5H), 5.12 (s, 2H), 4.5 (t, 1H), 4.4 (d, 1H), 4.15 (d, 1H), 3.45 (d, 1H), 3.0 (d, 1H), 2.9–2.6 (m, 2H), 2.5–2.3 (m, 2H), 2.2–1.8 (m 3H), 1.8–1.6 (m, 1H), 1.5–1.4 (m, 1H), 1.06 (s, 3H), 0.87 (s, 3H).

EXAMPLE 2j

3-Benzyloxycarbonylamino-5-(indan-1-ylmethanesulfonylamino)-4-oxo-pentanoic acid IR (KBr, cm$^{-1}$): 3314, 2930, 1704, 1530, 1318, 1266, 1145, 1059,746,698.

MS (AP+): 475.

EXAMPLE 2k

3-Benzyloxycarbonylamino-5-(9-fluoro-9H-fluoren-9-ylmethanesulfonylamino)-4-oxo-pentanoic acid MS (AP+): 521 (parent with loss of F–). NMR (F 19, CD$_3$OD, ppm) –77.1.

EXAMPLE 2l

3-Benzyloxycarbonylamino-5-(7,7-dimethyl-2-oxo-bicyclo[2.2.1]hept-1-(S)-ylmethanesulfonylamino)-4-oxo-pentanoic acid MS (AP–): 493. IR (KBr, cm$^{-1}$): 3374, 2961, 1733, 1522, 1455, 1416, 1330, 1274, 1204, 1179, 1146, 1052, 698.

EXAMPLE 2m (R)-3-Benzyloxycarbonylamino-5-(7,7-dimethyl-bicyclo[2.2.1]hept-1-ylmethane -sulfonylamino)-4-oxo-pentanoic acid

MS (APCI–): 479.2

The following compounds were prepared according to the procedure of Example 2a from the corresponding di, tri or tetrapeptide bromomethylketones and tert-butyl[(2-phenylethyl)sulfonyl]carbamate:

EXAMPLE 3a

3-[2-(2-Benzyloxycarbonylamino-3-methyl-butyrylamino)-propionylamino]-4-oxo-5-(2-phenyl-ethanesulfonylamino)-pentanoic acid Calculated for $C_{29}H_{38}N_4O_9S_1 \cdot 0.33CF_3COOH$: C, 54.26; H, 5.88; N, 8.53. Found: C, 54.26; H, 5.93; N, 8.55.

EXAMPLE 3b

3-[2-(2-Benzyloxycarbonylamino-4-carboxy-butyrylamino)-3-methyl -butyrylamino]-4-oxo-5-(2-phenyl-ethanesulfonylamino)-pentanoic acid

EXAMPLE 3c

3-{2-[4-Carboxy-2-(3-phenyl-propionylamino)-butyrylamino]-3-methyl-butyrylamino-}4-oxo-5-(2-phenyl-ethanesulfonylamino)-pentanoic acid Calculated for $C_{32}H_{42}N_4O_{10}S_1 \cdot 0.24CF_3COOH$: C, 55.56; H, 6.06; N, 7.98. Found: C, 55.56; H, 6.23; N, 8.07.

EXAMPLE 3d 3-(2-{2-[2-Acetylamino-3-(4-hydroxy-phenyl)-propionylamino]-4-carboxy-butyrylamino}-3-methyl-butyrylamino)-4-oxo-5-(2-phenyl-ethanesulfonylamino)-pentanoic acid (Sequence ID No. 1).

The following compounds were prepared according to the procedure of Example 2a from the corresponding protected di, tri or tetrapeptide bromomethylketones and tert-butyl[7,7-dimethyl-2-oxo-bicyclo[2.2.1]hept-1-ylmethanesulfonyl] carbamate:

EXAMPLE 4a 3-(2-Acetylamino-3-methyl-butyrylamino)-5-(7,7-dimethyl-2-oxo-bicyclo[2.2.1]hept-1-(S)-ylmethanesulfonylamino)-4-oxo-pentanoic acid MS (AP+): 502. IR (KBr, cm$^{-1}$): 3338, 2965, 1738, 1653, 1540, 1395, 1328, 1148.

EXAMPLE 4b 3-(2-Acetylamino-propylamino)-5-(7,7-dimethyl-2-oxo-bicyclo[2.2.1]hept 1-(S)-ylmethanesulfonylamino)-4-oxo-pentanoic acid

MS (AP−): 472.

EXAMPLE 4c

3-[2-(2-Benzyloxycarbonylamino-3-methyl-butyrylamino)-propionylamino]-5-(7,7-dimethyl-2-oxo-bicyclo[2.2.1]hept-1-ylmethanesulfonylamino)-4-oxo-pentanoic acid Calculated for $C_{31}H_{44}N_4O_{10}S_1 \cdot 0.30CF_3COOH$: C, 54.31; H, 6.39; N, 8.02. Found: C, 54.31; H, 6.51; N, 7.80.

EXAMPLE 4d

3-{2-[4-Carboxy-2-(3-phenyl-propionylamino)-butyrylamino-]3-methyl -butyrylamino}-5-(7,7-dimethyl-2-oxo-bicyclo[2.2.1]hept-1-ylmethanesulfonylamino)-4-oxo-pentanoic acid Calculated for $C_{34}H_{48}N_4O_{11}S_1 \cdot 0.43CF_3COOH$: C, 54.36; H, 6.34; N, 7.27. Found: C, 54.36; H, 6.57; N, 7.35.

EXAMPLE 4e 3-(2{2-[2-Acetylamino-3-(4-hydroxy-phenyl)-propionylamino-]4-carboxy-butyrylamino}-3-methyl-butyrylamino)-5-(7,7-dimethyl-2-oxo-bicyclo[2.2.1]hept-1-ylmethanesulfonylamino)-4-oxo-pentanoic acid (Sequence ID No. 2)

EXAMPLE 4f

3-[2-(2-Benzyloxycarbonylamino-4-carboxy-butyrylamino)-3-methyl-butyrylamino]-5-(7,7-dimethyl-2-oxo-bicyclo[2.2.1]hept-1-ylmethanesulfonylamino)-4-oxo-pentanoic acid The compounds of the present invention can also be synthesized by the following route:

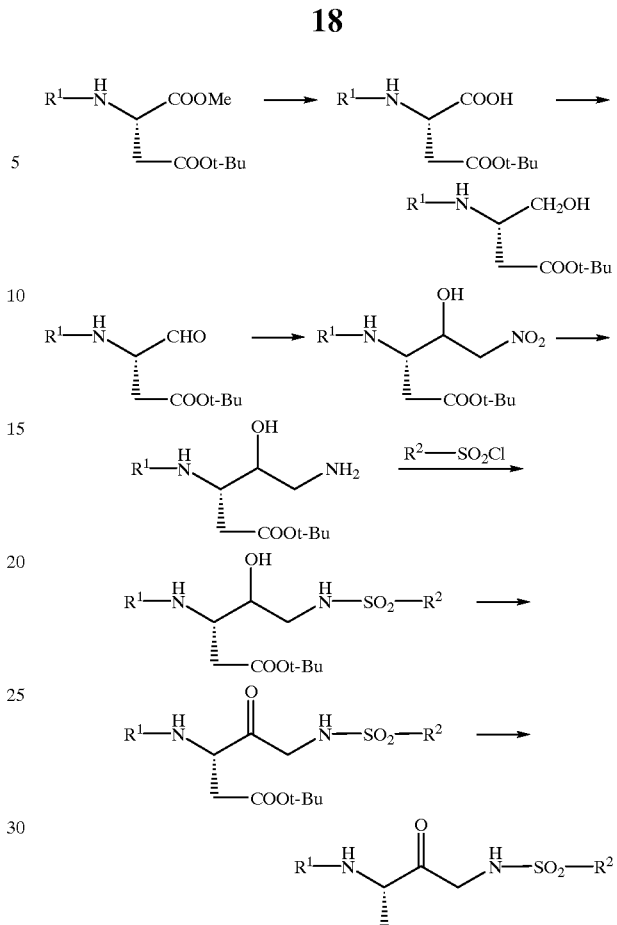

EXAMPLE 5a 3-(1,2,3,4-Tetrahydro-1-oxo-isoquinoline-2-yl)acetamino-5-benzenesulfonyl amino-4-oxo-pentanoic acid Step A To a solution of (1,2,3,4-tetrahydro-1-oxo-isoquinoline-2-yl)acetic acid (2.7 g, 13.0 mMol) prepared according to the procedure of Anderson W. K., et al., *J. Med. Chem,* 1988; 31: 2097 and H-Asp (OtBu)OMe×HCl(2.9 g, 12.0 mMol) in dimethylformamide (40 mL) was added at 0° C. 1-ethyl-3-(3'-dimethylamino-propyl) carbodiimide×HCl(2.5 g, 13.0 mMol) and triethylamine (4.05 g, 40 mMol). The mixture was stirred at room temperature for 16 hours. Most of the solvent was removed under reduced pressure, the residue was dissolved in ethyl acetate. The organic phase was washed successively with aqueous sodium hydrogencarbonate and water, dried over sodium sulfate, and concentrated to give 4.5 g of an amorphous residue.

The residue was dissolved in 40 mL of dioxane/water (1:1) and hydrolyzed in the presence of thymolphthalein by dropwise addition of 1N NaOH (12.0 mL). After evaporation of most of the dioxane and dilution with water the aqueous solution was extracted with ether, acidified with dilute HCl to pH 2–3, and the product extracted into ethyl acetate. The organic phase was washed with water, dried over sodium sulfate, and concentrated under reduced pressure to give 3.4 g of crystalline N-(1,2,3,4-tetrahydro-1-oxo-isoquinoline-2-yl)-acetyl aspartic acid, 4-tert-butyl ester.

Step B To a solution of N-(1,2,3,4-tetrahydro-1-oxo-isoquinoline-2-yl)-acetyl aspartic acid, 4-tert-butyl ester (3.1 g, 8.25 mMol) in 50 mL of tetrahydrofuran was added at −5° C. N-methylmorpholine (1.25 mL, 11.0 mMol) and isobutylchloroformate (1 eq). After 15 minutes between −5° C. and 0° C. the formed mixed anhydride was added at −78° C. to a suspension of sodium borohydride (0.75 g, 20 mMol) in 45 mL of tetrahydrofuran and 15 mL of methanol. After 2 hours at −40° C. the reaction was quenched by addition of 5.0 mL of acetic acid. Ethyl acetate/hexane (250 mL, 1:1) and water 30 mL was added. The organic phase was washed successively with saturated aqueous sodium hydrogen carbonate and water, dried over sodium sulfate, and concentrated under reduced pressure. Purification of the residue over silica (elution with dichloromethane/methanol 20:1) gave 3-(1, 2, 3, 4-tetrahydro-1-oxo-isoquinoline-2-yl)-acetamino-4-hydroxy-pentanoic acid, tert-butyl ester (2.3 g).

Step C

To a solution at −45° C. under nitrogen of dimethylsulfoxide (3.72 mL, 52.4 mMol) in dichloromethane was added dropwise via syringe oxalyl chloride (2.5 g, 28.8 mMol) followed by N-(1,2,3,4-tetrahydro-1-oxo-isoquinoline-2-yl)-acetamino-4-hydroxy-pentanoic acid, tert-butyl ester (6.88 g, 24.0 mMol). After 30 minutes the reaction was quenched by addition of diisopropylethyl amine (12.4 mL, 72.0 mMol) and partitioned between ethyl acetate (800 mL) and water (80 mL). The organic phase was washed successively with 1N sodium hydrogen sulfate and water, dried over sodium sulfate, and concentrated under reduced pressure to give 4.8 g of 3-(1,2,3,4-tetrahydro-1-oxo-isoquinoline-2-yl)-acetamino-4-oxo-pentanoic acid, tert-butyl ester.

Step D

To 1.15 g (10.0 mMol) of KOtBu (potassium tertbutoxide) in dimethylformamide (30 mL) at 0° C. under nitrogen and nitromethane (1.75 mL, 32.5 mMol) was added 3-(1,2,3,4-tetrahydro-1-oxo-isoquinoline-2-yl)-acetamino-4-oxo-pentanoic acid, tert-butyl ester (3.6 g, 10.0 mMol). After 3 hours at 0° C. the reaction was quenched by addition of 1.5 mL of acetic acid and partitioned between ethyl acetate (200 mL) and water (20 mL). The organic phase was washed with saturated aqueous sodium hydrogen carbonate and water, dried over sodium sulfate, and concentrated under reduced pressure. Purification of the residue over silica (elution with dichloromethane/methanol 20:1) gave 2.7 g of 3-(1, 2, 3, 4-tetrahydro-1-oxo-isoquinoline-2-yl)-acetamino-4-hydroxy-5-nitro-pentanoic acid, tert-butyl ester as 1:1 mixture of diastereomers.

Step E

A mixture of 3-(1,2,3,4-tetrahydro-1-oxo-isoquinoline-2-yl)-acetamino-4-hydroxy-5-nitro-pentanoic acid, tert-butyl ester (2.55 g, 6.05 mMol) and 10% Pd on charcoal (1.5 g) in 100 mL of methanol containing 5 mL of 10% aqueous acetic acid was hydrogenated at room temperature for 4 hours. Filtration and evaporation of the solvent under reduced pressure gave of 3-(1,2,3,4-tetrahydro-1-oxo-isoquinoline-2-yl)-acetamino-5-amino-4-hydroxy-pentanoic acid, tert-butyl ester hydroacetate (2.7 g).

Step F

To a solution of 3-(1,2,3,4-tetrahydro-1-oxo-isoquinoline-2-yl)-acetamino-5-amino-4-hydroxy-pentanoic acid, tert-butyl ester hydroacetate (1.31 g, 2.9 mMol) in 15 mL of dichloromethane at 0° C. was added benzenesulfonychloride (0.45 mL, 3.5 mMol) followed by dropwise addition of N-methylmorpholine (0.8 mL, 9 mMol). The solution was left at room temperature for 16 hours, then diluted with ethyl acetate (100 mL). The organic phase was washed successively with sodium hydrogen carbonate and water, dried over sodium sulfate, and concentrated under reduced pressure. Chromatography over silica (elution with dichloromethane/methanol 15:1) gave 3-(1,2,3,4-tetrahydro-1-oxo-isoquinoline-2-yl)-acetamino-5-benzenesulfonylamino-4-hydroxy-pentanoic acid, tert-butyl ester (1.05 g).

Step G

To 3-(1,2,3,4-tetrahydro-1-oxo-isoquinoline-2-yl)-acetamino-5-benzenesulfonylamino-4-hydroxy-pentanoic acid, tert-butyl ester (0.9 g, 1.7 mMol) in 20 mL of dichloromethane was added 1.1.1-triacetoxy-1.1-dihydro-1.2-benziodoxol-3-(1H)-one (Dess Martin periodinane, 1.08 g, 2.5 mMol). After 2 hours at room temperature the reaction mixture was diluted with ether, filtered, washed with sodium hydrogen carbonate and water, dried over sodium sulfate, and concentrated under reduced pressure. Chromatography over silica (elution with dichloromethane/methanol 15:1) gave 3-(1,2,3,4-tetrahydro-1-oxo-isoquinoline-2-yl)-acetamino-5-benzenesulfonylamino-4-oxo-pentanoic acid, tert-butyl ester (0.45 g).

Step H

A solution of 3-(1, 2, 3, 4-tetrahydro-1-oxo-isoquinoline-2-yl)-acetamino-5-benzenesulfonylamino-4-hydroxy-pentanoic acid, tert-butyl ester (0.44 g, 0.48 mMol) and 15 mL of trifluoroacetic acid in 15 mL of dichloromethane was stirred at room temperature for 1 hour. The solution was concentrated under reduced pressure. Crystallization from dichloromethane/ether/hexane gave 0.17 g of 3-(1,2,3,4-tetrahydro-1-oxo-isoquinoline-2-yl)-acetamino-5-benzenesulfonylamino-4-oxo-pentanoic acid.

The following compounds were also prepared according to the procedure of Example 5 Steps F–H from the corresponding sulfonyl chlorides:

EXAMPLE 5b (S)-5-(Bicyclo[2.2.1]hept-1-ylmethanesulfonylamino)-4-oxo-3-[2-(1-oxo-3,4-dihydro-1H-isoquinolin-2-yl)-acetylamino]-pentanoic acid

EXAMPLE 5c (S)-4-Oxo-3-[2-(1-oxo-3,4-dihydro-1H-isoquinolin-2-yl)-acetylamino]-5-(2-phenyl-ethanesulfonylamino)-pentanoic acid

EXAMPLE 5d

4-Oxo-3-[2-(1-oxo-3,4-dihydro-1H-isoquinolin-2-yl)-acetylamino]-5-phenylethanesulfonylamino-pentanoic acid

EXAMPLE 6a

3-[2-(2-Benzyloxycarbonylamino-4-tert-butylcarbonyl-butyrylamino)-3-methyl-butyrylamino]-5-bromo-4-oxo-pentanoic acid tert-butyl ester A solution of Z-Glu(OtBu)ValAsp(OtBu)-OH(14.9 g, 24.6 mmol) and 4-methylmorpholine (2.7 mL, 24.6 mmol) in 200 mL of THF at ca. −40° C. (dry ice CH$_3$CN bath) was treated with iso-butyl chloroformate (3.2 mL, 24.6 mmol). Solid immediately formed. The sample was stirred for 15 minutes, then treated with cold diazomethane (300 mL of an ether solution, freshly prepared from Diazald). The sample was stirred at room temperature for 2 hours, cooled to 0° C. and quenched by dropwise addition of a 48% hydrobromic acid-acetic acid solution (35 mL of each). The ice-bath was removed, the sample was stirred at room temperature for 30 minutes, then extracted with ethyl acetate-water (500 mL of each). The organic extract was washed with water, sat. NaHCO₃ and brine solutions, dried (MgSO₄), filtered and concentrated. The residue was crystallized from dichloromethane-hexanes to give 10.5 g (63%) of 3-[2-(2-benzyloxy-carbonylamino-4-tert-butoxycarbonyl-butyrylamino)-3-methyl-butyrylamino]-5-bromo-4-oxo-pentanoic acid tert-butyl ester (Z-Glu(OtBu)ValAsp(OtBu)CH2Br) as a white solid.

Analysis Calculated for $C_{31}H_{46}BrN_3O_9$(684.636): C, 54.39; H, 6.77; N, 6.14. Found: C, 54.24; H, 6.63; N, 6.08.

Also prepared according to the procedure of Example 6a from the corresponding peptides were:

EXAMPLE 6b 3-(2-Acetylamino-3-methyl-butyrylamino)-5-bromo-4-oxo-pentanoic acid tert-butyl ester

EXAMPLE 6c 3-(2-Acetylamino-pronylamino)-5-bromo-4-oxo-pentanoic acid tert-butyl ester

EXAMPLE 6d

3-[2-(3-Phenyl-propionylamino-4-tert-butoxycarbonyl-butyrylamino)-3-methyl-butyrylamino]-5-bromo-4-oxo-pentanoic acid tert-butyl ester

EXAMPLE 6e

3-[2-(2-Benzyloxycarbonylamino-3-methyl-butyrylamino)-propionylamino]-5-bromo-4-oxo-pentanoic acid

Inhibition Studies

Compounds of Formula I and II are inhibitors of ICE as demonstrated by measurement of $K_i$ ($\mu$M) and $IC_{50}$ ($\mu$M) using the protocol described herein. ICE (0.24 nNM final concentration) is added to 400 $\mu$L of HGDE buffer (100 mM HEPES, 20% glycerol, 5 mM DTT, 0.5 mM EDTA) containing 15 $\mu$FM substrate (Ac-Tyr-Val-Ala-Asp-AMC (Sequence ID No. 3); $K_M$=15 $\mu$M) plus vehicle (DMSO) or inhibitor at concentrations bracketing the $K_i$. Substrate hydrolysis is monitored for 300 seconds by observing the fluorescence of released AMC using excitation at 380 nm and emission at 460 nm. Mean rates of substrate hydrolysis are evaluated by linear-regression analysis of the fluorescence vs time traces. To evaluate $K_i$, plots of percent inhibition vs inhibitor concentration are fit by non-linear regression to a reversible, competitive model:

$$\% \text{Inhibition} = \frac{100 * [I]}{[I] + K_i * \left(1 + \frac{[S]}{K_M}\right)}$$

where the competition factor $(1+[S]/K_M)=2$.

ICE Colorimetric Dose-Response ($IC_{50}$) Assay

Diluted inhibitor stocks are prepared by two-fold serial dilution from a primary stock whose concentration is selected (based on screening results or on prior attempts at $IC_{50}$ evaluation) to achieve approximately 95% inhibition in the most concentrated well. Aliquots of each dilution are transferred to a microtitre plate in triplicate.

ICE enzyme is diluted to approximately 24 nM in HGE buffer (100 mM HEPES pH 7.5, 0.5 mM EDTA, 20% glycerol, 0.1% Bovine Serum Albumin (BSA)), and activated by adding dithiothreitol (DTT) to a final concentration of 5 mM. The activated enzyme is then aliquoted into wells containing inhibitor or vehicle, and the plate is preincubated for 60 minutes at ambient temperature.

Substrate (Ac-Tyr-Val-Ala-Asp-pNA) (Sequence ID No. 4) is added to each well to a final concentration of 50 $\mu$M, and plates are placed in the microtitre plate-reader thermostated to 25° C. Beginning 5 minutes after addition of substrate, absorbance (405 nm) of wells is monitored for 1 hour, and activity is calculated as the mean rate of change in absorbance during this interval.

Ich-2 (Caspase-4) Colorimetric Dose-Response ($IC_{50}$) Assay

Inhibition of Ich-2 enzyme is assayed as described above for ICE, except that enzyme is used at 64 nM, and 60 $\mu$M of the Ich-2-specific substrate Ac-Leu-Glu-Val-Asp-pNA Sequence ID No. 5 is used instead of the ICE substrate Ac-Tyr-Val-Ala-Asp-pNA Sequence ID No. 6.

The results of these assays are shown below in Table 1.

TABLE 1

| Example Number | ICE Ki ($\mu$M) | ICE $IC_{50}$ ($\mu$M) | Ich-2 $IC_{50}$ (Caspase-4) ($\mu$M) |
|---|---|---|---|
| 2a | 11 | 73 | 96 |
| 2b | 32 | 245 | — |
| 2c | 14 | 168 | 124 |
| 2a | 11.0 | 73.0 | 445.0 |
| 2b | 34.5 | 245.0 | 8591.0 |
| 2c | 18.0 | 168.0 | 2339.0 |
| 2d | 37.0 | 291.0 | |
| 2e | 735.0 | 1833.0 | |
| 2f | 22.0 | 174.0 | 1008.0 |
| 2g | 33.0 | 136.0 | 314.0 |
| 2h | 16.0 | 55.6 | 199.0 |
| 2i | 30.1 | 25.0 | 59.0 |
| 2j | 65.0 | 194.0 | 159.0 |
| 2k | 22.0 | | |
| 2l | 1.4 | 28.0 | 935.0 |
| 2m | 2.8 | 35.3 | |
| 3a | 0.007 | 0.072 | 18.0 |
| 3b | 0.013 | 0.025 | 4.2 |
| 3c | 0.0051 | 0.009 | 3.4 |
| 3d | 0.0078 | 0.003 | 0.9 |
| 4a | 0.27 | 7.6 | |
| 4c | 0.001 | 0.015 | 8.5 |
| 4d | 0.0016 | 0.003 | 1.6 |
| 4e | 0.00011 | 0.002 | 0.7 |
| 4f | 0.00061 | 0.002 | 3.2 |
| 5a | 105.0 | 586.0 | |
| 5b | 20.0 | 165.0 | 252.0 |
| 5c | 45.0 | 371.0 | |
| 5d | 27.0 | 234.0 | |

| | |
|---|---|
| HEPES = | 4-(2-hydroxymethyl)-1-piperazine ethane sulfonic acid |
| DTT = | Dithiothreitol |
| EDTA = | Ethylene diamine tetra acetic acid |
| AMC = | 7-amino-4-methyl coumarin |
| Tyr = | Tyrosine |
| Val = | Valine |
| Ala = | Alanine |
| Asp = | Aspartic Acid |
| pNA = | Para nitroaniline |
| LEU = | Leucine |
| Glu = | Glutamic acid |
| Me = | Methyl |
| t-Bu = | Tert butyl |

What is claimed is:

1. A compound of Formula I

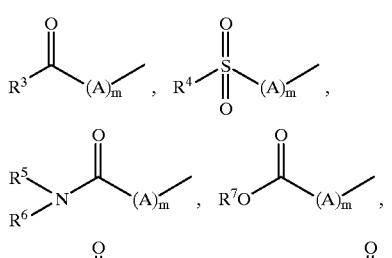

wherein $R^1$ is

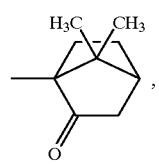

$R^3$ is hydrogen,
$C_1$–$C_6$ alkyl,
—$(CH_2)_n$ aryl, or
—$(CH_2)_n$ heteroaryl;

$R^4$ is $C_1$–$C_6$ alkyl,
—$(CH_2)_n$ aryl, or
—$(CH_2)_n$ heteroaryl;

$R^5$ and $R^6$ are each independently hydrogen,
$C_1$–$C_6$ alkyl,
—$(CH_2)_n$ aryl, or
—$(CH_2)_n$ heteroaryl;

$R^7$ is $C_1$–$C_6$ alkyl,
—$(CH_2)_n$ aryl, or
—$(CH_2)_n$ heteroaryl;

each n is independently 0 to 6;

each m is independently 0, 1, 2, or 3;

A is alanine, leucine, isoleucine, proline, phenylalanine, glycine, tyrosine, serine, threonine, tryptophan, cysteine, methionine, valine, asparagine, glutamine, aspartic acid, lysine, glutamic acid, arginine, or histidine;

$R^2$ is —$(CH_2)n$—Z; and

Z is aryl, heteroaryl, cycloalkyl, $C_1$–$C_6$ alkyl,

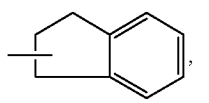 , 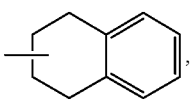 ,

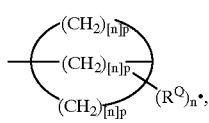

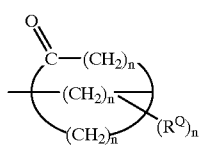

wherein each $R^Q$ is independently hydrogen or $C_1$–$C_6$ alkyl, and each p is independently 1, 2 or 3, fluorenyl, substituted flourenyl, substituted aryl, substituted heteroaryl, or substituted cycloalkyl, and the pharmaceutically acceptable salts, esters, amides and prodrugs thereof.

2. A compound according to claim 1 wherein $R^1$ is

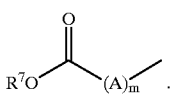

3. A compound according to claim 1 wherein $R^1$ is

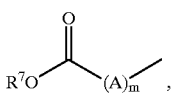 , m is 0, and $R^7$ is —$(CH_2)_n$ aryl.

4. A compound according to claim 1 wherein $R^1$ is

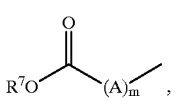 , m is 0, and $R^7$ is —$CH_2$ aryl.

5. A compound according to claim 1 wherein $R^2$ is —$(CH_2)_n$ aryl.

6. A compound according to claim 5 wherein aryl is phenyl or naphthyl.

7. A compound according to claim 1 wherein $R^2$ is —$(CH_2)_n$-cycloalkyl.

8. A compound according to claim 1 wherein $R^1$

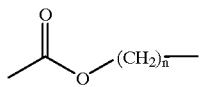

phenyl or —$SO_2$-phenyl.

9. A compound according to claim 1 wherein $R^2$ is

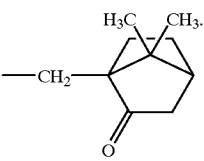

10. A compound according to claim 1 wherein $R^2$ is

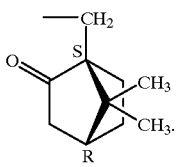

11. A compound of the Formula I

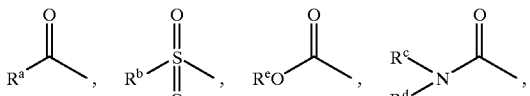

I wherein $R^2$ is —$CH_2CH_2$-aryl, —$CH_2$-cycloalkyl, —$CH_2CH_2$-cycloalkyl, or —$CH_2CH_2$-heteroaryl;

$R^1$ is

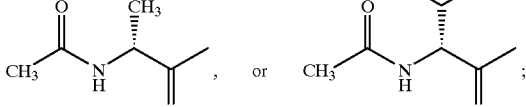

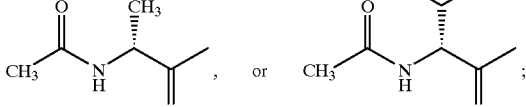

$R_a$ is —$(CH_2)_n$-aryl or —$(CH_2)_n$ heteroaryl;

$R^b$ is aryl or heteroaryl;

$R^c$ is —$CH_2$ aryl or aryl;

$R^d$ is hydrogen or $C_1$–$C_6$ alkyl;

$R^e$ is —$CH_2$ aryl or —$CH_2$ heteroaryl; and the pharmaceutically acceptable salts, esters, amides, and prodrugs thereof.

12. A compound according to claim 11 wherein $R^1$ is

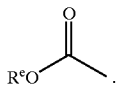 .

13. A compound according to claim 11 wherein $R^1$ is

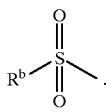

14. A compound according to claim 11 wherein $R^e$ is —$(CH_2)_n$ aryl.

15. A compound according to claim 14 wherein aryl is phenyl or naphthyl.

16. A compound according to claim 13 wherein $R^b$ is aryl.

17. A compound according to claim 16 wherein is aryl is phenyl.

18. The compounds:
3-Benzyloxycarbonylamino-4-oxo-5-(2-phenylethanesulfonylamino)-pentanoic acid;
3-Benzyloxycarbonylamino-4-oxo-5-(3-phenyl-propane-1-sulfonylamino)-pentanoic acid;
3-Benzyloxycarbonylamino-4-oxo-5-phenylmethanesulfonyl-amino-pentanoic acid;
5-Benzenesulfonylamino-3-benzyloxycarbonylamino-4-oxo-pentanoic acid;
3-Benzyloxycarbonylamino-5-methanesulfonylamino-4-oxo-pentanoic acid;
3-Benzyloxycarbonylamino-5-(naphthalene-1-sulfonylamino)-4-oxo-pentanoic acid;
3-Benzyloxycarbonylamino-5-(2-cyclohexyl-ethanesulfonylamino)-4-oxo-pentanoic acid;
3-Benzyloxycarbonylamino-5-(2-naphthalen-1-yl-ethanesulfonylamino)-4-oxo-pentanoic acid;
3-Benzyloxycarbonylamino-5-(7,7-dimethyl-2-oxo-bicyclo [2.2.1]hept-1-(R)-ylmethanesulfonylamino)-4-oxo-pentanoic acid;
3-Benzyloxycarbonylamino-5-(indan-1-ylmethanesulfonylamino) -4-oxo-pentanoic acid;
3-Benzyloxycarbonylamino-5-(9-fluoro-9H-fluoren-9-ylmethanesulfonylamino)-4-oxo-pentanoic acid;
3-Benzyloxycarbonylamino-5-(7,7-dimethyl-2-oxo-bicyclo[2.2.1]hept-1-(S)-ylmethanesulfonylamino)-4-oxo-pentanoic acid;
3-(2-Acetylamino-3-methyl-butyrylamino)-5-(7,7-dimethyl-2-oxo-bicyclo[2.2.1]hept-1-(S)-ylmethanesulfonylamino)-4-oxo-pentanoic acid;
3-(2-Acetylamino-propylamino)-5-(7,7-dimethyl-2-oxo-bicyclo[2.2.1]hept-1-(S)-ylmethanesulfonylamino)-4-oxo-pentanoic acid;
3-(1,2,3,4-tetrahydro-1-oxo-isoquinoline-2-yl)-acetanino-5-benzenesulfonylamino-4-oxo-pentanoic acid;
(S)-5-(Bicyclo[2.2.1]hept-1-ylmethanesulfonylamino)-4-oxo-3-[2-(1-oxo-3,4-dihydro-1H-isoquinolin-2-yl)-acetylamino]-pentanoic acid;
(S)-4-Oxo-3-[2-(1-oxo-3,4-dihydro-1H-isoquinolin-2-yl)-acetylamino]-5-(2-phenyl-ethanesulfonylamino)-pentanoic acid; and
4-Oxo-3-[2-(1-oxo-3,4-dihydro-1H-isoquinolin-2-yl)-acetylamino]-5-phenylethanesulfonylamino-pentanoic acid.

19. A pharmaceutically acceptable composition that contains a compound of claim 1.

20. A pharmaceutically acceptable composition that contains a compound of claim 11.

21. A compound of the Formula II

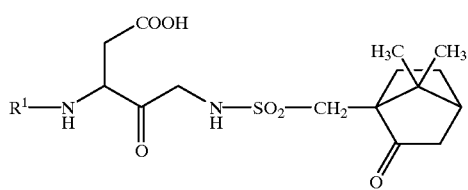

wherein
$R^1$ is

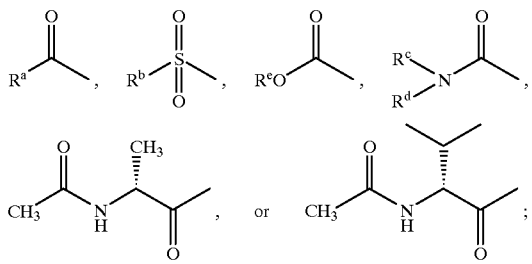

$R^a$ is —$(CH_2)_n$-aryl or —$(CH_2)_n$ heteroaryl;
$R^b$ is aryl or heteroaryl;
$R^c$ is —$CH_2$ aryl or aryl;
$R^d$ is hydrogen or $C_1$–$C_6$ alkyl;
$R^e$ is —$CH_2$ aryl or —$CH_2$ heteroaryl; and the pharmaceutically acceptable salts, esters, amides, and prodrugs thereof.

22. A compound according to claim 21 wherein $R^1$ is

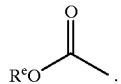

23. A compound according to claim 21 wherein $R^1$ is

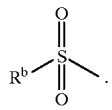

24. A compound according to claim 21 wherein $R^e$ is —$(CH_2)_n$ aryl.

25. A compound according to claim 21 wherein aryl is phenyl or naphthyl.

26. A compound according to claim 21 wherein $R^b$ is aryl.

27. A compound according to claim 26 wherein is aryl is phenyl.

28. The compounds:
3-[2-(2-Benzyloxycarbonylamino-3-methyl-butyrylamino)-propionylamino]-4-oxo-5-(2-phenyl-ethanesulfonylamino)-pentanoic acid;
3-[2-(2-Benzyloxycarbonylamino-4-carboxy-butyrylamino)-3-methyl-butyrylamino]-4-oxo-5-(2-phenyl-ethanesulfonylamino)-pentanoic acid;
3-{2-[4-Carboxy-2-(3-phenyl-propionylamino)-butyrylamino]-3-methyl-butyrylamino}-4-oxo-5-(2-phenyl-ethanesulfonylamino)-pentanoic acid;
3-[2-(2-Benzyloxycarbonylamino-3-methyl-butyrylamino) -propionylamino]-5-(7,7-dimethyl-2- oxo-bicyclo[2.2.1]hept-1-ylmethanesulfonylamino)-4-oxo-pentanoic acid;

3-[2-(2-Benzyloxycarbonylamino-4-carboxy-butyrylamino)-3-methyl-butyrylamino]-5-(7,7-dimethyl-2-oxo-bicyclo[2.2.1]hept-1-ylmethanesulfonylamino)-4-oxo-pentanoic acid;

3{-2-[4-Carboxy-2-(3-phenyl-propionylamino)-butyrylamino]-3-methyl-butyrylamino}-5-(7,7-dimethyl-2-oxo-bicyclo[2.2.1]hept-1-ylmethanesulfonylamino)-4-oxo-pentanoic acid;

3-(2-{2-[2-Acetylamino-3-(4-hydroxy-phenyl)-propionylamino]-4-carboxy-butyrylamino}-3-methyl-butyrylamino)-5-(7,7-dimethyl-2-oxo -bicyclo[2.2.1]hept-1-ylmethanesulfonylamino)-4-oxo-pentanoic acid (Sequence ID No. 2); and 3-(2-{2-[2-Acetylamino-3-(4-hydroxy-phenyl)-propionylamino]4-carboxy-butyrylamino}-3-methyl-butyrylamino)-4-oxo-5-(2-phenyl-ethanesulfonylamino)-pentanoic acid (Sequence ID No. 1).

\* \* \* \* \*

SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<221> NAME/KEY: UNSURE
<222> LOCATION: (4)
<223> OTHER INFORMATION: (2-phenyl-ethanesulfonylamino) attached to 3'
      end
<220> FEATURE:
<223> OTHER INFORMATION: Description of Artificial Sequence: Chemically
      synthesized

<400> SEQUENCE: 1

Tyr Glu Val Asp
  1

<210> SEQ ID NO 2
<211> LENGTH: 4
<212> TYPE: PRT
<213> ORGANISM: Artificial Sequence
<220> FEATURE:
<221> NAME/KEY: UNSURE
<222> LOCATION: (4)
<223> OTHER INFORMATION: (7,7-dimethyl-2-oxobycyclo[2.2.1]hept-1-
      lmethanesuylfonylamino) attached to 3' end
<220> FEATURE:
<223> OTHER INFORMATION: Description of Artificial Sequence: Chemically
      synthesized

<400> SEQUENCE: 2

Tyr Glu Val Asp
  1

<210> SEQ ID NO 3
<211> LENGTH: 4
<212> TYPE: PRT
<213> ORGANISM: Artificial Sequence
<220> FEATURE:
<221> NAME/KEY: UNSURE
<222> LOCATION: (1)..(4)
<223> OTHER INFORMATION: Acetyl group attached to 5' end and AMC group
      attached to 3' end
<220> FEATURE:
<223> OTHER INFORMATION: Description of Artificial Sequence: Chemically
      synthesized

<400> SEQUENCE: 3

Tyr Val Ala Asp
  1

<210> SEQ ID NO 4
<211> LENGTH: 4
<212> TYPE: PRT
<213> ORGANISM: Artificial Sequence
<220> FEATURE:
<221> NAME/KEY: UNSURE
<222> LOCATION: (1)..(4)
<223> OTHER INFORMATION: Acetyl group attached to 5' end and pNA group
      attached to 3'end
<220> FEATURE:
<223> OTHER INFORMATION: Description of Artificial Sequence: Chemically
      synthesized

<400> SEQUENCE: 4

Tyr Val Ala Asp
  1

```
<210> SEQ ID NO 5
<211> LENGTH: 4
<212> TYPE: PRT
<213> ORGANISM: Artificial Sequence
<220> FEATURE:
<221> NAME/KEY: UNSURE
<222> LOCATION: (1)..(4)
<223> OTHER INFORMATION: Acetyl group attached to 5' end and pNA group
      attached to 3' end
<220> FEATURE:
<223> OTHER INFORMATION: Description of Artificial Sequence:  Chemically
      synthesized

<400> SEQUENCE: 5

Leu Glu Val Asp
  1

<210> SEQ ID NO 6
<211> LENGTH: 4
<212> TYPE: PRT
<213> ORGANISM: Artificial Sequence
<220> FEATURE:
<221> NAME/KEY: UNSURE
<222> LOCATION: (1)..(4)
<223> OTHER INFORMATION: Acetyl group attached to 5' end and pNA group
      attached to 3' end
<220> FEATURE:
<223> OTHER INFORMATION: Description of Artificial Sequence:  Chemically
      synthesized

<400> SEQUENCE: 6

Tyr Val Ala Asp
```